(12) United States Patent
Yang (10) Patent No.: US 11,004,538 B2
(45) Date of Patent: May 11, 2021

(54) METHOD AND DEVICE FOR DETECTING CHROMOSOMAL STRUCTURAL ABNORMALITIES

(71) Applicant: BGI GENOMICS CO., LTD., Shenzhen (CN)

(72) Inventor: Chuanchun Yang, Shenzhen (CN)

(73) Assignee: BGI GENOMICS CO., LTD., Shenzhen (CN)

( * ) Notice: Subject to any disclaimer, the term of this patent is extended or adjusted under 35 U.S.C. 154(b) by 1197 days.

(21) Appl. No.: 14/890,989

(22) PCT Filed: May 15, 2013

(86) PCT No.: PCT/CN2013/075622
§ 371 (c)(1),
(2) Date: Nov. 13, 2015

(87) PCT Pub. No.: WO2014/183270
PCT Pub. Date: Nov. 20, 2014

(65) Prior Publication Data
US 2016/0085911 A1 Mar. 24, 2016

(51) Int. Cl.
*G16B 30/00* (2019.01)
*G16B 40/00* (2019.01)
*C12Q 1/6869* (2018.01)

(52) U.S. Cl.
CPC ........... *G16B 30/00* (2019.02); *C12Q 1/6869* (2013.01); *G16B 40/00* (2019.02)

(58) Field of Classification Search
None
See application file for complete search history.

(56) References Cited

FOREIGN PATENT DOCUMENTS

| | | |
|---|---|---|
| CN | 101561845 A | 10/2009 |
| CN | 101914628 A | 12/2010 |
| CN | 102409099 A | 4/2012 |
| CN | 102789553 A | 11/2012 |
| RU | 2471871 | 1/2013 |
| WO | 2011143231 A2 | 11/2011 |
| WO | 2012088348 A2 | 6/2012 |
| WO | 2012097474 A1 | 7/2012 |
| WO | 2014/183270 A1 | 11/2014 |

OTHER PUBLICATIONS

Guo et al. The effect of strand bias in Illumina short-read sequencing data, BMC Genomics 2012, 13:666 at http://www.biomedcentral.com/1471-2164/13/666.*
Volfovsky et al. A clustering method for repeat analysis in DNA sequences Genome Biology 2001,2(8):research0027.1-0027.11 Published: Aug. 1, 2001.*
Talkowski et al., "Next-Generation Sequencing Strategies Enable Routine Detection of Balanced Chromosome Rearrangements for Clinical Diagnostics and Genetic Research", American Journal of Human Genetics, vol. 88, No. 4, pp. 469-481 (Mar. 17, 2011).
Sindi et al., "An Integrative Probabilistic Model for Identification of Structural Variation in Sequencing Data", Genome Biology, vol. 13, No. 3, 25 pages (2012).
Abel et al., "Detection of Structural DNA Variation from Next Generation Sequencing Data: A Review of Informatic 4approaches", Cancer Genetics, vol. 206, No. 12, pp. 432-440 (2013).
Rausch et al., "DELLY: structural variant discovery by integrated paired-end and split-read analysis", Bioinformatics 2012;28:i333-i339.
Abel et al., "Detection of gene rearrangements in targeted clinical next generation sequencing", J Mol Diagn. 2014;16(4):405-17.

* cited by examiner

*Primary Examiner* — Jospeh Woitach
(74) *Attorney, Agent, or Firm* — Ice Miller LLP (57) ABSTRACT

A method and a device for detecting chromosomal structural abnormalities are provided. The method includes acquiring a whole genome sequencing result of a target individual, that is, multiple pairs of Reads located at two ends of chromosome fragments are determined; aligning the sequencing result with a reference sequence to obtain an abnormal match set, which includes Read pairs that have two Read sequences matched respectively to different chromosomes of the reference sequence; clustering the Read sequences in the abnormal match set based on the positions matched thereto; and filtering the resultant clusters by using, for example, preset requirements associated with compactness and others, and obtaining the filtered result, clusters, for determining the occurrence of translocation-type chromosomal structural abnormity.

10 Claims, 4 Drawing Sheets

METHOD AND DEVICE FOR DETECTING CHROMOSOMAL STRUCTURAL ABNORMALITIES

CROSS REFERENCE TO RELATED APPLICATION

This application is a Section 371 of International Application No. PCT/CN2013/075622, filed May 15, 2013, which was published in the Chinese language on Nov. 20, 2014 under International Publication No. WO 2014/183270 A1, and the disclosure of which is incorporated herein by reference.

BACKGROUND

Technical Field

The present invention relates to the technical field of genomics and bioinformatics technologies, and more particularly to a method and a device for detecting chromosomal structural abnormalities.

Related Art

Currently, the commonly used chromosome examination methods include the following.

Karyotype analysis, for example G-banding karyotype analysis, determines chromosomal structural abnormalities based on the distribution of 400 to 600 BANDs, and thus generally can detect the abnormalities on chromosomal level only. The method may detect the deletion or repetition of above 5 Mbp in the best situations, but fails to detect much smaller fragments (<5 M). Moreover, the method necessitates the culture of living cells, and the cells are required to stay alive.

Fluorescence in situ hybridization (FISH) can detect the deletion, repetition, and balanced translocation of much smaller fragments. However, the chromosome fragment to be detected is required to be predetermined, to prepare the corresponding probe. As such, the method is limited by probe design. FISH is frequently used for validation of detection results, due to its failure in detection of unknown regions.

Microarray method includes two probe methods. One is designed based on single nucleotide polymorphisms (SNPs), and the other is designed based on CNV. Therefore, the method suffers from the similar limitations to FISH.

With the continuous development of whole genome sequencing technologies, the sequencing cost is continuously lowered, so that generalization of whole genome sequencing may become possible. It is necessary to investigate means of finding chromosomal structural abnormalities based on whole genome sequencing results.

SUMMARY

According to an aspect of the present invention, a method for detecting chromosomal structural abnormalities is provided, comprising: acquiring a whole genome sequencing result of a target individual, where the whole genome sequencing result includes multiple pairs of Reads, each pair of Reads consists of two Read sequences located respectively at two ends of a chromosome fragment determined, and each pair of Reads is derived separately from the positive and negative strands of the corresponding chromosome fragment, or both from the positive or negative strand of the corresponding chromosome fragment; aligning the sequencing result with a reference sequence, to obtain an abnormal match set, where the abnormal match set includes a first type of Read pairs in accordance with the description that two Read sequences in the first type of Read pair are matched respectively to different chromosomes of the reference sequence; clustering the Read sequences in the abnormal match set based on the positions matched thereto, where each cluster contains single-end Read sequences from a group of Read pairs, and the corresponding other-end Read sequences reside in another cluster; filtering the resultant clusters, including calculating the compactness of each cluster and filtering off the clusters having a compactness failed to meet a preset requirement R-va and the clusters paired therewith, and obtaining the filtered result clusters containing the first type of Read pairs, for determining the occurrence of translocation-type chromosomal structural abnormity.

According to another aspect of the present invention, a device for detecting chromosomal structural abnormalities is provided, which comprises a data input unit, configured to input data; a data output unit, configured to output data; a storage unit containing an executable program therein and configured to store data; and a processor, in data connection with the data input unit, the data output unit, and the storage unit, and configured to execute the executable program stored in the storage unit, where the execution of the program includes performing the method for detecting chromosomal structural abnormalities.

According to a further aspect of the present invention, a computer readable storage medium is provided, which is configured to store a program executable by a computer. It should be understood by those of ordinary skill in the art that when the program is executed, all or part of the steps of the method for detecting chromosomal structural abnormalities may be performed by relevant hardware under instruction. The storage medium may include a read only memory, a random access memory, a magnetic disk or an optical disc.

According to the method of the present invention, the translocation-type chromosomal structural abnormity can be screened out by obtaining Read pairs matched to different chromosomes through alignment of the whole genome sequencing result with the reference sequence, and the effectiveness and reliability of the obtained result is further improved by clustering and filtering, thus obtaining results of analytical significance.

BRIEF DESCRIPTION OF THE DRAWINGS

The above and/or other additional aspects and advantages of the present invention become apparent and comprehensible from the description of detailed embodiments in connection with accompanying drawings, in which.

DETAILED DESCRIPTION

According to an embodiment of the present invention, a method for detecting chromosomal structural abnormalities is provided, which includes the following steps.

Step 1. Obtain a Whole Genome Sequencing Result of a Target Individual

The sequencing result includes paired Reads, each pair of Reads consists of two Read sequences located respectively at two ends of a chromosome fragment determined, and each pair of Reads is derived separately from the positive and negative strands of the corresponding chromosome fragment, or both from the positive or negative strand of the corresponding chromosome fragment.

Figure 1:
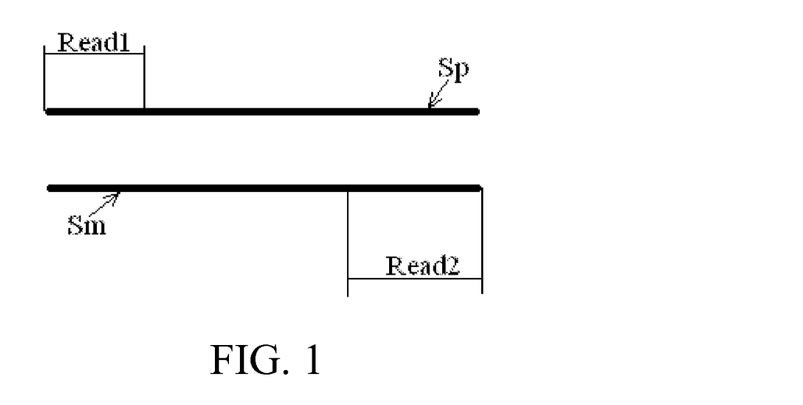
FIG. 1 is a schematic view of a pair of Reads obtained by paired-end sequencing according to an embodiment of the present invention.

The chromosome fragment determined is generally obtained by segmenting the chromosome sample from a target individual, and then used for preparation of a corresponding library according to the selected sequencing method. The sequencing method may be selected depending on the sequencing platform, including, but not limited to, Complete Genomics (CG), Illumina/Solexa, ABI/SOLiD, and Roche 454, and the preparation of a single-end or paired-end sequencing library is performed according to the selected sequencing platform. According to a specific embodiment of the present invention, paired-end sequencing may be performed. The two Read sequences Read1 and Read2 in each pair of Reads obtained are derived separately from the positive strand Sp and the negative strand Sm of the corresponding chromosome fragment, as shown in FIG. 1. The length L-r1 of Read1 may be the same or different from the length L-r2 of Read2. Definitely, where the single-end sequencing method used can fully acquire the sequence of the whole chromosome fragment, it may be feasible to segment a suitable length of sequence respectively from the two ends of the fully acquired sequence, to form a pair of Reads. In this case, the two Read sequences in each pair of Reads are both derived from the positive or negative strand of the corresponding chromosome fragment. In this embodiment, there are no limitations on the specific sequencing method selected.

In the present invention, the size of the library used for sequencing is designated as L-lib, and generally, a library with an L-lib of 100 to 1000 bp is referred to as small-fragment library, and a library with an L-lib of 2 K, 5 K-6 K, 10 K, 20 K, and 40 Kbp is referred to as large-fragment library. In the present invention, the size of L-lib is not limited. However, with the construction quality of the library ensured, a longer library generally contributes to the acquisition of valid result. Therefore, it is preferred that L-lib≥300 bp. Generally, a large-fragment library of for example 5 Kbp or a small-fragment library of for example 500 bp may be used. To allow the sequencing result to have a good abundance, the sequencing depth may be selected to be above 2× for the large-fragment library, and to be above 5× for the small-fragment library. To avoid the waste of data, the sequencing depth is preferably 2× for the large-fragment library, and 5× for the small-fragment library. It should be noted that because most of the specific data involved in the present invention is statistically significant, any numerical value that is precisely expressed represents a range, that is, an interval within ±10% of the numerical value, unless it is otherwise particularly stated. The description is not repeated hereinafter.

L-r1 and L-r2 are preferably greater than or equal to 25 bp, because where L-r1 and L-r2 are less than 25 bp, the unique alignment rate decreases, such that the complexity is increased in subsequent acquisition of the alignment results. L-r1 and L-r2 need not to be too large, to avoid the waste of data. Therefore, L-r1 and L-r2 are preferably 50 bp. L-r1 and L-r2 have no maximum value limitations, and may be varied with the development of the sequencing technology. For example, L-r1 and L-r2 are generally not higher than 150 bp based on existing sequencing technologies.

Step 2. Align the Sequencing Result with a Reference Sequence

The reference sequence used is a known sequence, and may be any reference template previously obtained from the category to which the target individual belongs. For example, if the target individual is human, the reference sequence may be HG19 provided by national center for biotechnology information (NCBI). Further, a resource repository comprising more reference sequences may be pre-configured, and a more close reference sequence is selected depending on the sex, race, geographical region, and other factors of the target individual before sequence alignment, to promote the acquisition of a more accurate detection result. During alignment, according to the alignment parameters set, a pair of Reads is allowed to have n mismatches at most, where n is preferably 1 or 2. If more than n mismatches occur in the pair of Reads, the pair of Reads is considered to be unable to align to the reference sequence, or if the mismatched n bases are all located in one of the pair of Reads, the Read sequence in the pair of Reads is considered to be unable to align to the reference sequence. Specifically, various alignment software for example Short Oligonucleotide Analysis Package (SOAP), bwa, and samtools etc may be used during alignment. This is not limited in this embodiment.

Depending on the alignment of Read pairs, the following categories may be obtained.

(I) Normal match set *.pair, includes Read pairs in accordance with the description that two Read sequences Read1 and Read2 in the Read pair are matched to the same chromosome of the reference sequence, the positive and negative strand relation of the positions matched thereto is in agreement with that in the Read pair, and the length L-pr of the chromosome fragment calculated according to the positions matched thereto deviates from L-lib by a value less than a preset threshold V-lib. V-lib is preferably from 5%×L-lib to 15%×L-lib, and more preferably 10%×L-lib. The threshold is empirically set based on the standard deviation of the library size. Empirically, the standard deviation of a small-fragment library is about 15 bp, and the standard deviation of a large-fragment library is about 50 bp. A deviation of L-pr from L-lib in the range of 3-fold standard deviations is deemed to be suitable, for example, it is considered that L-pr is suitably in the range of 455-545 bp for a library of 500 bp.

Based on *.pair, the quantitative distribution of Read pairs in accordance with the position matched thereto may be obtained, for example, the number of Reads per unit length (RPU) may be calculated statistically. The corresponding unit length may be set according to L-lib, for example, set to 1.5-4 time of L-lib. If L-lib is 500 bp, the unit length may set to 1 Kbp, and in this case, RPU may be designated as RPK. The variation of RPU compared with the average value, for example, whether the variation is above a preset threshold V-rm, may assist in the determination of the occurrence of structural abnormalities, thereby increasing the analysis accuracy of the result. Preferably, V-rm is 10 to 30% and more preferably 20%. Further, the average RPU may be obtained through statistical calculation or from estimation. For example, the average RPU may be estimated by a formula: sequencing depth×(unit length/L-lib). If RPU is not needed, *.pair does not have to be obtained.

(II) Abnormal match set *.sin, includes three types of Reads in accordance with the descriptions below.

Figure 2:
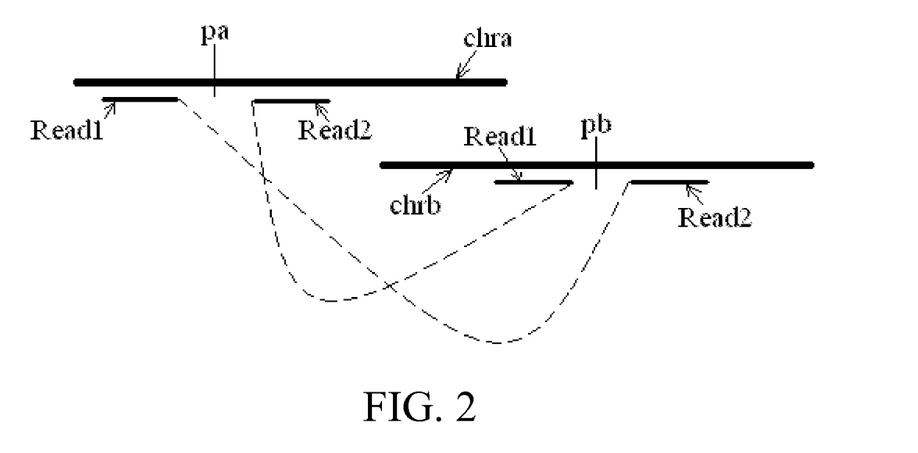
FIG. 2 is a schematic view of a first type of Read pairs of abnormal match according to an embodiment of the present invention.

In a first type, two Read sequences in a Read pair are respectively matched to different chromosomes of the reference sequence. This type of Read pairs correlate with translocation-type structural abnormality, for example balanced and unbalanced translocation. FIG. 2 shows a situation of balanced translocation, in which Read1 in a pair of Reads is matched to the chromosome chra, and Read2 is matched to the chromosome chrb, and the case is the opposite for another pair of Reads. In FIG. 2, the dash line connecting Read1 and Read2 indicates the head-to-tail position relation of Read1 and Read2 in the chromosome fragment (the same below), and pa and pb denote potential positions of breakpoints respectively, where "breakpoint" means boundary point of occurrence of structural abnormality on a chromosome.

Figure 3:
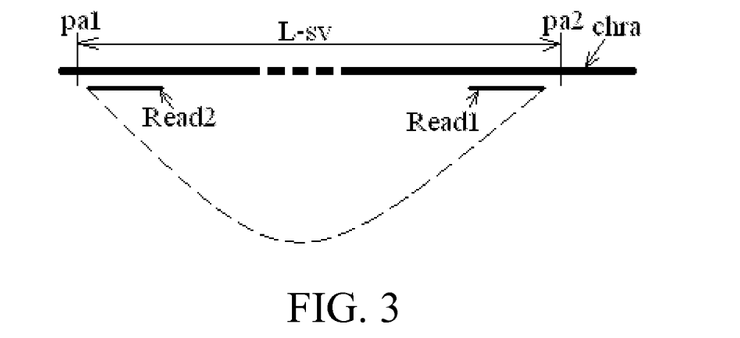
FIG. 3 is a schematic view of a second type of Read pairs of abnormal match according to an embodiment of the present invention.

In a second type, two Read sequences in a Read pair are matched to the same chromosome of the reference sequence, but L-pr is negative. This type of Read pairs correlate with tandem repetition-type structural abnormality. As shown in FIG. 3, Read1 and Read2 in a pair of Reads are both matched to the chromosome chra; however, the head-to-tail position relation of the positions matched thereto is opposite to that of Read1 and Read2 in the chromosome fragment. In FIG. 3, pa1 and pa2 denote the starting and terminating positions of the potential repeat fragment respectively, L-sv denotes the length of the repeat fragment, and the dash line in the middle portion of chra denotes omitted length (the same below).

Figure 4:
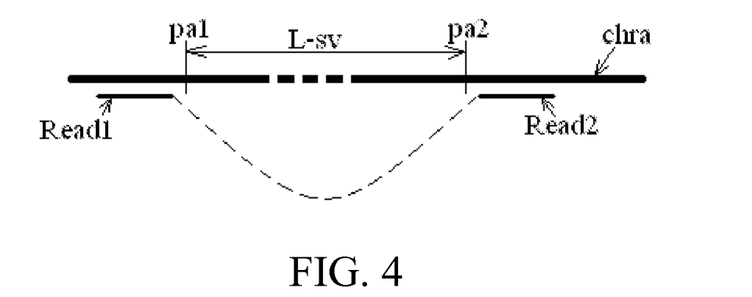
FIG. 4 is a schematic view of a third type of Read pairs of abnormal match according to an embodiment of the present invention.

In a third type, two Read sequences in a Read pair are matched to the same chromosome of the reference sequence; however, L-pr is greater than L-lib, and the deviation is above the preset threshold V-lib. This type of Read pairs correlate with deletion-type structural abnormality. As shown in FIG. 4, Read1 and Read2 in a pair of Reads are both matched to the chromosome chra, and the head-to-tail position relation of the positions matched thereto is the same as that of Read1 and Read2 in the chromosome fragment, but the distance goes beyond a suitable range. In FIG. 4, pa1 and pa2 denote the starting and terminating positions of potentially deleted fragment respectively, and L-sv denotes the length of the deleted fragment.

Because different types of Read pairs in the abnormal match set represent different types of chromosomal structural abnormalities that may occur respectively, the Read pairs of abnormal match of the types above may not have to be acquired totally, as desired by detection. For example, where merely the translocation-type structural abnormality needs to be detected, the first type of Read pairs may be acquired from the alignment result only. Also, the abnormal match set does not exclusively include the above three types of Read pairs, and Read pairs or a Read sequence in the Read pairs that do not belong to the normal match set and can be matched to the reference sequence are embraced in the abnormal match set. The manifestations of different types of abnormal matches may be correlated with corresponding chromosomal structural abnormalities that may occur by those of ordinary skill in the art. Furthermore, considering the influence of potential noise and other interferences, the positive and negative strand match or mismatch may be not discriminated in the abnormal match set.

(III) Unmatch set *.unmap, includes Read sequences that are unable to match to the reference sequence, and that may be paired (both are unable to match to the reference sequence) or be single-end Read sequences (the other-end Read sequences are able to match to the reference sequence).

The single-end Read sequences existing in *.unmap are further used for breakpoint assembly after acquiring the result clusters, to obtain a more accurate breakpoint range. If breakpoint assembly is not needed, *.unmap does not have to be obtained.

Step 3. Cluster the Read Sequences in *.sin Based on the Positions Matched Thereto Clustering may be achieved by using various clustering algorithms, which are not limited in this embodiment. For example, a simple approach is to divide the clusters based on a set minimum inter-cluster distance V-cl. That is, Read sequences ranked according to positions are searched. Starting from a first Read sequence, if the distance between a second Read sequence and the first Read sequence is less than V-cl, they are divided in the same cluster. Then, the search is continued from the second Read sequence, until the distance between an nth Read sequence and an (n−1)th Read sequence is greater than V-cl. Then, a second cluster may be divided starting from the nth Read sequence, and the process is repeatedly performed through all the Read sequences. During clustering, this may be performed according to the position of Read matched on the chromosome, regardless of the positive or negative strand.

Figure 5:
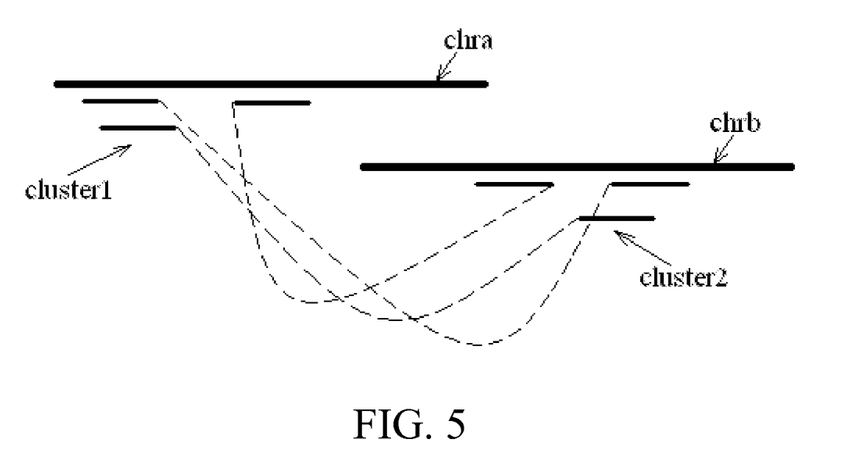
FIG. 5 is a schematic view of a pair of clusters located on different chromosomes according to an embodiment of the present invention.

After clustering, each cluster contains single-end Read sequences from a group of Read pairs, and correspondingly the other-end Read sequences are located in another cluster. Therefore, the two clusters are referred to as a pair of clusters. FIG. 5 is a schematic view of a pair of clusters formed by cluster1 and cluster2 located on different chromosomes respectively. Definitely, paired clusters may be located on the same chromosome. To make the analysis after clustering significant, each cluster preferably includes more than two Reads. In case that the distance between an individual Read and a preceding and following Read is greater than V-cl, said outlier may be discarded.

V-cl is at least L-lib. If the set value is too low, the number of candidate clusters is too large, and the number of the Read sequences in the cluster is too small, which are inconvenient for the subsequent screening and filtering, and may also lead to increased false positive results. If the set value is too high, the determination of breakpoints may be inconvenient, and the range of breakpoints is enlarged. Therefore, V-cl is preferably 10 Kbp. Depending on different clustering algorithms used, V-cl may have different specific meanings. For example, V-cl may be the distance between the centers of gravity of two adjacent clusters, or the distance between two closest Reads in position in two adjacent clusters.

Step 4. Filter the Resultant Clusters

Filtering aims at removing various potential interferences to the greatest extent, for example sample contamination, sequencing errors, alignment errors, and noise, such that the result can reflect real chromosomal structural abnormalities to the largest degree. Therefore, the filtering conditions may be set depending on actual requirements and the types of potential interferences. In this embodiment, the following filtering means are preferably provided, which may be used alone or in combination of several of them in practical application.

(I) By virtue of the compactness of the clusters—The compactness of each cluster is calculated, and the clusters that have a compactness failed to meet a preset requirement R-va and the clusters paired therewith are filtered off. The compactness of each cluster may be calculated by using various mathematical methods available. For example, the compactness may be indicated by variance. The variance of the position of each read in a cluster to the center or center of gravity of the cluster is calculated, and the smaller the variance is, the higher the compactness will be. Preferably, during the calculation of the compactness of each cluster, Read sequences located at two ends in the range of 5 to 25% and preferably 20% in length of the cluster may be excluded, to reduce the influence of peripheral data on the calculation result. Preferably, R-va may be set to a fixed threshold, for example, the variance is required to be below the fixed threshold. Or otherwise, R-va is set to be an elimination rate. For example, the ranks of the variances in all the clusters are required to fall within a preset lowermost interval. For example, R-va is set such that the ranks of the variances in all the clusters fall within a lowermost interval of 2%-10% and preferably 5%.

The compactness of the cluster reflects the stability of Read distribution, and indicates whether the Read sequences are concentrated in a small interval. Generally, a real structural variation may be swallowed up in a large number of "environmental noises". However, the influence of "environmental noises" on the whole genome is substantially uniform, and thus appears to have an essentially even distribution in the whole sequence (which of course, may be affected by, for example, the content of GC (Guanine and Cytosine), and others). In a site where a real structural variation takes place, Read sequences in the cluster appear to have a substantially normal distribution. Therefore, the compactness, for example, variance, can well reflect the inter-cluster difference.

(II) By virtue of the linear correlation of paired clusters—The linear correlation of two paired clusters is calculated, and the paired clusters that have a linear correlation failed to meet a preset requirement R-li are filtered off. The linear correlation of a pair of clusters may be calculated by using various mathematical methods available. For example, the coefficient of correlation of two clusters is calculated, and the higher the coefficient of correlation is, the higher the linear correlation will be. Preferably, R-li may be set to a fixed threshold, for example, the coefficient of correlation is required to be above the fixed threshold. Or otherwise, R-li is set to be an elimination rate. For example, the ranks of the coefficients of correlation in all the clusters are required to fall within a preset uppermost interval. For example, R-li is set such that the ranks of the coefficients of correlation in all the clusters fall within an uppermost interval of 2%-10% and preferably 5%.

The linear correlation highly emphasizes the consistency in distribution of Read sequences in the paired clusters, that is, indicates whether the two-end Read sequences in paired Reads have the substantially consistent distribution. Therefore, the linear correlation can better reflect the distribution in paired clusters.

In a preferred embodiment, a good result is achieved by filtering the candidate clusters using the compactness, for example, variance of the clusters, and the linear correlation of the clusters in combination.

(III) By virtue of a control set of normal samples—The paired clusters are aligned with a control set comprising a plurality of normal samples, and the paired clusters that have a normal sample hitting count reaching a preset threshold V-con are filtered off. The normal samples refer to a set of result clusters obtained by subjecting other normal individuals that belong to the same category as the target individual to the "alignment-clustering-filtering" processes as described above. For ease of alignment, all the Read sequences in the cluster may be merged into one, and thus a pair of merged numerical values is generated from paired clusters (which resembles a pair of Reads). Alignment is performed with the merged numerical value pairs. By collecting a control set comprising a large number of normal samples, the frequency of the result clusters occurred in normal individuals can be obtained. If a certain result cluster has a high frequency of occurrence, it may be suggested that the result cluster may result from sample quality, experimental process, sequencing process or environmental noise, and does not indicate that the sample actually undergoes such a structural variation per se. Such a result cluster is a co-false positive result obtained by analyzing different samples with the same method, and should be removed. Therefore, the probability of false positive events may be further reduced by filtering the result clusters using a control set, which contributes to the acquisition of true analysis result of structural variation. V-con may be determined depending on the construction modes and features of normal samples. For example, the proportion of V-con to the number of normal samples in the control set may be 3-10%, and preferably 5-6%. For example, if the control set contains 90 normal samples, 5 hits are considered to reach the threshold.

(IV) By virtue of other auxiliary parameters—The auxiliary parameters include various parameters helpful in further confirmation and distinguishment of the types of structural abnormalities or in understanding the details of structural abnormalities, for example, the number of mismatches generated during alignment, the number of Read pairs supporting the clusters, RPU value of relevant region obtained based on *.pair, whether the clusters are located in an N region, and others. The auxiliary parameters may be used by the following two ways. 1. The auxiliary parameters are used as filtering conditions. Filtering requirements associated with the auxiliary parameters are set to filter off the clusters failed to meet the requirements directly. 2. The auxiliary parameters are used as reference basis assisting in determination. The auxiliary parameters are provided with the result clusters, and then determination is conducted through manual analysis. Therefore, the contents in this section may be used in Step 4 (for filtering), or in Step 5 (for assisting in manual analysis). In this embodiment, the specific ways of using the auxiliary parameters are not limited. Some auxiliary parameters and relation with result analysis thereof are exemplified below. In practical application, the auxiliary parameters may be set as filtering conditions following the descriptions below, or as a basis for assisting in determination through manual analysis. Different auxiliary parameters may be used in combination or alone.

(1) Number of mismatches.—The average mismatches of Read pairs in paired clusters are generally no more than 1 or 2, that is, each pair of Reads are allowed to have 1 or 2 mismatches, and preferably no more than 1 mismatch. The parameter need not to be taken into account, if the match requirement in alignment is set based on this. If the setting in alignment is less strict, for example, it is set that 2 mismatches are allowed to occur, filtering or determination may be further performed using the parameter during the acquisition of the result cluster, for example it is set that 1 mismatch is allowed to occur on average.

(2) Number of Read pairs supporting the clusters, that is, the number of Read pairs contained in paired clusters—In principle, it will be better if the parameter is higher. Generally, the judgment basis may be set to be in consistent with or slightly less (for example, take an integral value) than the normalized value of the sequencing depth, where the normalized value of the sequencing depth=sequencing depth× (range of influence of L-lib on breakpoints/L-lib)×(average spans at two ends of paired clusters/L-lib). The "range of influence of L-lib on breakpoints" is generally higher than "the sum of spans at two ends of paired clusters", and generally fluctuates at an average that is 2 times of L-lib, for example, fluctuates between 1-4 times of L-lib. When specifically set, the range of the parameter may be appropriately widened or narrowed as desired by practical situation.

(3) RPU value of relevant region obtained based on *.pair—Different types of structural abnormalities generally have different influence on RPU. For example, in the case of balanced translocation, RPU at two lateral sides of the breakpoints does not vary significantly; however, in the case of deletion- or repetition-type structural abnormality, RPU of the region between the breakpoints decreases or increases considerably. Therefore, the RPU value of a relevant region may be further used for confirming or assisting in the determination of the occurrence of chromosomal structural abnormalities.

For example, for the clusters containing the first type of Read pairs, if balanced translocation is determined according to the relation between the Read pairs in the clusters (see Section I of Step 5 below for details), the variation of RPU at two lateral sides of the breakpoints from an average is not higher than V-rm; and if unbalanced translocation is determined according to the relation between the Read pairs in the clusters (see Section I of Step 5 below for details), RPU at the side of the breakpoints departing from the result clusters is below the average, and the variation is higher than V-rm.

For the clusters containing the second type of Read pairs, RPU of the region between the breakpoints is above the average, and the variation is higher than V-rm.

For the clusters containing the third type of Read pairs, RPU of the region between the breakpoints is below the average, and the variation is higher than V-rm.

When RPU is used as a basis for assisting in determination through manual analysis, RPU of a relevant region may be presented in the form of a graph, a table or in other readily identifiable form. Alternatively, the variation of RPU in the whole region is presented in the form of a graph, a table, or the like, for promoting the understanding of the overall conditions by the operator.

(4) Whether the cluster is located in an N region—Empirically, the alignment of Reads in vicinity of the N region (comprising areas of centromere and telomere) is more complex than other regions. If the obtained clusters are not located in the N region, it is considered that determination can be made according to the acquired information. If the obtained clusters are located in the N region, more careful validation may be required. For example, the final determination is made by combined use of filtering conditions and auxiliary parameters, or in conjunction with other external data, for example, the phenotype of the target individual, and/or the result from further accurate sequencing (for example Sanger sequencing) of the breakpoints.

Step 5. Data Analysis of the Filtered Result Clusters

The presence of the result clusters obtained after filtering reflects the potential occurrence of corresponding types of chromosomal structural abnormalities. Therefore, this step is not necessary where only potential structural abnormalities are required to be found. For the purpose of obtaining more detailed information regarding structural abnormalities, the obtained result clusters may be further subjected to data analysis. Depending on different types of result clusters, the following ways of analysis may be adopted.

(I) Translocation-Type Chromosomal Structural Abnormity (the First Type of Reads)

The result clusters containing the first type of Read pairs are searched, and if two adjacent Read sequences have opposite positions in respective Read pairs, the range between positions that the two Read sequences are matched to is taken as a range of breakpoints. This situation generally correlates with balanced translocation, in which the Read sequences in the same cluster are distributed at two lateral sides of the breakpoints.

If no such Read sequences exist, the position of an innermost Read sequence is acquired, and the range obtained by extending inward from the position by a preset length is taken as a range of breakpoints. The innermost Read sequence means that where the cluster includes exclusively left-end Read sequences, the Read sequence on the very right is the innermost Read sequence; and where the cluster includes exclusively right-end Read sequences, the Read sequence on the very left is the innermost Read sequence. This situation generally correlates with unbalanced translocation, in which the Read sequences in the same cluster are distributed at one lateral side of the breakpoints. The span of the range of breakpoints extending from the innermost Read sequence may be determined according to L-lib, L-r1/L-r2, the sequencing depth, and others, and may be for example 0.5-2 times of L-lib and generally no more than 2 times of L-lib.

FIG. 2 shows a situation of balanced translocation. An obtained pair of result clusters (only two Read sequences are depicted in each cluster, and the others are regarded to be omitted) has a distribution as shown in FIG. 2, one result cluster is located in vicinity of the position pa on the chromosome chra, and the result cluster paired therewith is located in vicinity of the position pb on the chromosome chrb. Since in the cluster on chra, Read1 is a left-end Read sequence of the chromosome fragment from which it is derived, and the adjacent Read2 is a right-end Read sequence of the chromosome fragment from which it is derived, it is considered that the breakpoint pa of chra is located between Read1 and Read2, and the same analysis applies to chrb.

Based on the above data analysis, the result data output for potential translocation-type structural abnormity may includes numberings of two chromosomes (on which the result clusters are located respectively) potentially having translocation-type structural abnormity, position ranges of two ends of paired result clusters (position ranges of boundaries of two ends of the clusters on the two chromosome, from which the spans of the two ends of the clusters may be corresponding obtained), range of breakpoints obtained after analysis, and others. Relevant parameters generated during filtering and other auxiliary parameters may also be output alongside, for example, respective compactness of a pair of result clusters, degree of linear correlation of the pair of result clusters, number of Read pairs supporting the pair of result clusters, and graph and table presenting the variation in RPU at two lateral sides of the breakpoints.

(II) Tandem Repetition-Type Chromosomal Structural Abnormity (the Second Type of Read Pairs)

The result clusters containing the second type of Read pairs are searched, the range between two positions matched thereto that are farthest in distance in the paired clusters is taken as an occurrence range of repetition, and the range obtained by extending outward from the two positions respectively by a preset length that is for example 0.5-2 times of L-lib is taken as a range of breakpoints (the starting and terminating points of the repeat fragment).

FIG. 3 shows a situation of tandem repetition. Two ends of paired result clusters (only one Read sequence is depicted in each cluster, and the others are regarded to be omitted) both fall within the range between the starting and terminating points of the repeat fragment, and thus it is considered that the starting and terminating points of the repeat fragment are located in a range extending outward from the Read sequences (in which the two Read sequences do not necessarily belong to a pair of Reads) at the outermost position of the two ends of the clusters.

Compared with translocation-type structural abnormity, the repetition-type structural abnormity has substantially the same types of result data output, except that the numberings of the chromosomes at two ends of the clusters are the same, and data indicating the estimated length of the repeat fragment may be output as well.

(III) Deletion-Type Chromosomal Structural Abnormity (the Third Type of Read Pairs)

The result clusters containing the third type of Read pairs are searched, the range between two positions matched thereto that are closest in distance in the paired clusters is taken as an occurrence range of deletion, and the range obtained by extending inward from the two positions respectively by a preset length that is for example 0.5-2 times of L-lib is taken as a range of breakpoints (the starting and terminating points of the deleted fragment).

FIG. 4 shows a situation of fragment deletion. Two ends of paired result clusters (only one Read sequence is depicted in each cluster, and the others are regarded to be omitted) both fall outside the range between the starting and terminating points of the deleted fragment, and thus it is considered that the starting and terminating points of the deleted fragment are located in a range extending inward from the Read sequences (in which the two Read sequences do not necessarily belong to a pair of Reads) that are closest at the two ends of the clusters.

Compared with repetition-type structural abnormity, the deletion-type structural abnormity has substantially the same types of result data output, except that the output data indicating the estimated length of the fragment between the breakpoints represents the length of the deleted fragment.

Step 6. Breakpoint Assembly

To further reduce the range of breakpoints, breakpoint assembly may be conducted by using the data from *.unmap. For example, single-end Read sequences (that are able to single-end matched to the reference sequence, and may be designated to *.sin during alignment) in a range set peripherally to the determined range of breakpoints (for example 0.5-2 times of L-lib) are obtained, and Read sequences paired therewith are retrieved from *.unmap as patch sequences. All the Patch sequences are truncated into N sections, and N is preferably 2. Then, the sub-sequences obtained after truncating the patch sequences are aligned with the reference sequence again. The breakpoint region is assembled according to the result of normal match.

In practical use, the value of N may be rationally set according to the length of Lr1/Lr2. Where the sequence length is less than 25 bp, the unique alignment rate is caused to decrease considerably. Accordingly when the value of N is set, it may be taken in mind that the length of the truncated sub-sequence is not or not obviously less than 25 bp.

After breakpoint assembly, the range of breakpoints may be effectively reduced. On basis of this, a probe may be further prepared according to the range of positions that the breakpoints reside, and the accurate positions of breakpoints may finally be obtained by means of other accurate sequencing, for example Sanger sequencing, for further carrying out the study on breakpoints. If the range of breakpoints need not to be reduced, this step may be omitted.

It may be understood by those of ordinary skill in the art that all or part of the steps of the methods provided in the embodiments above may be performed by relevant hardware under instruction of a program that may be stored in a computer readable storage medium, including a read only memory, a random access memory, a magnetic disk or an optical disc.

According to another aspect of the present invention, a device for detecting chromosomal structural abnormalities is further provided, which includes a data input unit, configured to input data; a data output unit, configured to output data; a storage unit, configured to store data and containing an executable program therein; and a processor, in data connection with the data input unit, the data output unit, and the storage unit, and configured to execute the executable program stored in the storage unit, wherein the execution of the program includes performing all or part of the steps of the methods provided in the embodiments above.

Hereinafter, the operation result of a specific detection method according to the present invention is described in detail in connection with specific target individual. In the detection process, the specific parameters used are set as follows.

1. L-lib is 500 bp, and PE50 sequencing (pair-end sequencing, in which L-r1 and L-r2 are roughly 50 bp) is employed.

2. HG19 from NCBI is used as a reference sequence, and the sequencing result is aligned by SOAP software.

3. V-lib is ±45 bp, V-rm of RPK is 20%, V-cl is 10 Kbp (the intercluster distance is defined as the distance between two closest Read sequences), the minimum Read number in the cluster is 2, R-va is set such that the ranks of the variances in all the clusters fall within a lowermost interval of 5% (in calculation of the variance, read sequences located at two ends in the range of 20% in length of the cluster are excluded), R-li is set such that the ranks of the coefficients of correlation in all the clusters fall within an uppermost interval of 5%, the control set includes 90 normal samples, and V-con is 5.

Experimental Example I

This example gives study on a family of criduchat syndrome. In this example, the two target individuals belong to the same family, in which "FA" represents the father, and "SON" represents the son.

1. Whole-genome sequencing was respectively conducted on the two target individuals at a low multiplier, in which the sequencing depth of "FA" was 2.2, and 3.1 for "SON".

2. Then, the sequencing results of the two target individuals were aligned respectively with the reference sequence HG19 by using the SOAP alignment software, to obtain two files FA.sin and SON.sin.

Figure 6:
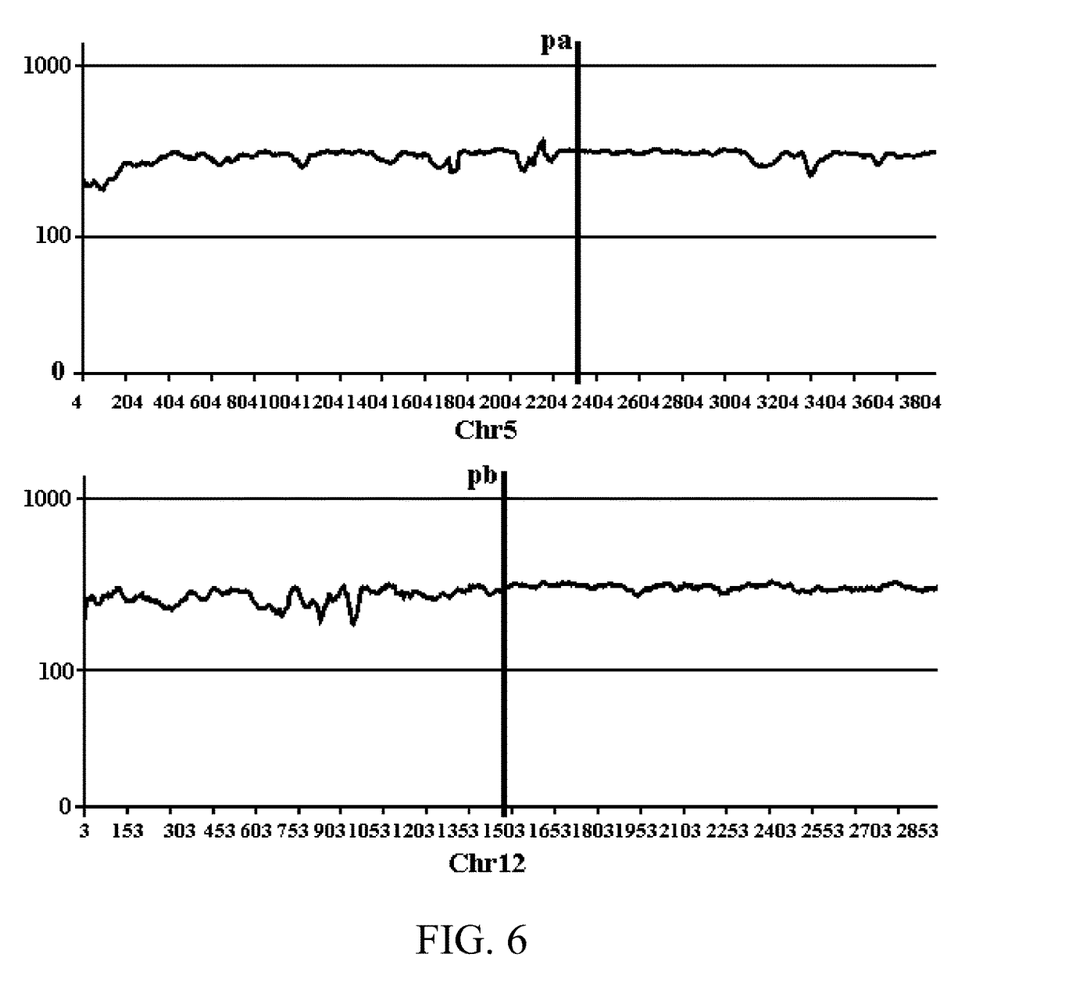
FIG. 6 is a schematic view of RPK for "FA" in Experimental Example 1 according to an embodiment of the present invention.

3. The two files FA.sin and SON.sin were clustered, filtered, and analyzed, to obtain the following result clusters and relevant output parameters:

"FA":

numbering of two chromosomes on which paired result clusters reside: chr12, chr5 position ranges of two ends of paired result clusters: 14779615-14780233, 23314785-23314205 spans of two ends of paired result clusters: 618, 580 number of Read pairs supporting the pair of result clusters: 5 compactness (variance) of the left and right ends: 90.59, 87.01 whether the clusters are located in an N region: not range of breakpoints: chr12:14779968-14780233, chr5: 23314205-23314455 variation in RPK of relevant regions on the chromosomes—In FIG. 6, the horizontal axis represents the position (unit: 10 Kbp) on the chromosome, and the longitudinal axis represents RPK. The curve is plotted on basis of the data from FA.pair, and pa and pb represent the positions of breakpoints. It can be seen from FIG. 6 that the variation in RPK of "FA" is insignificant.

Figure 7:
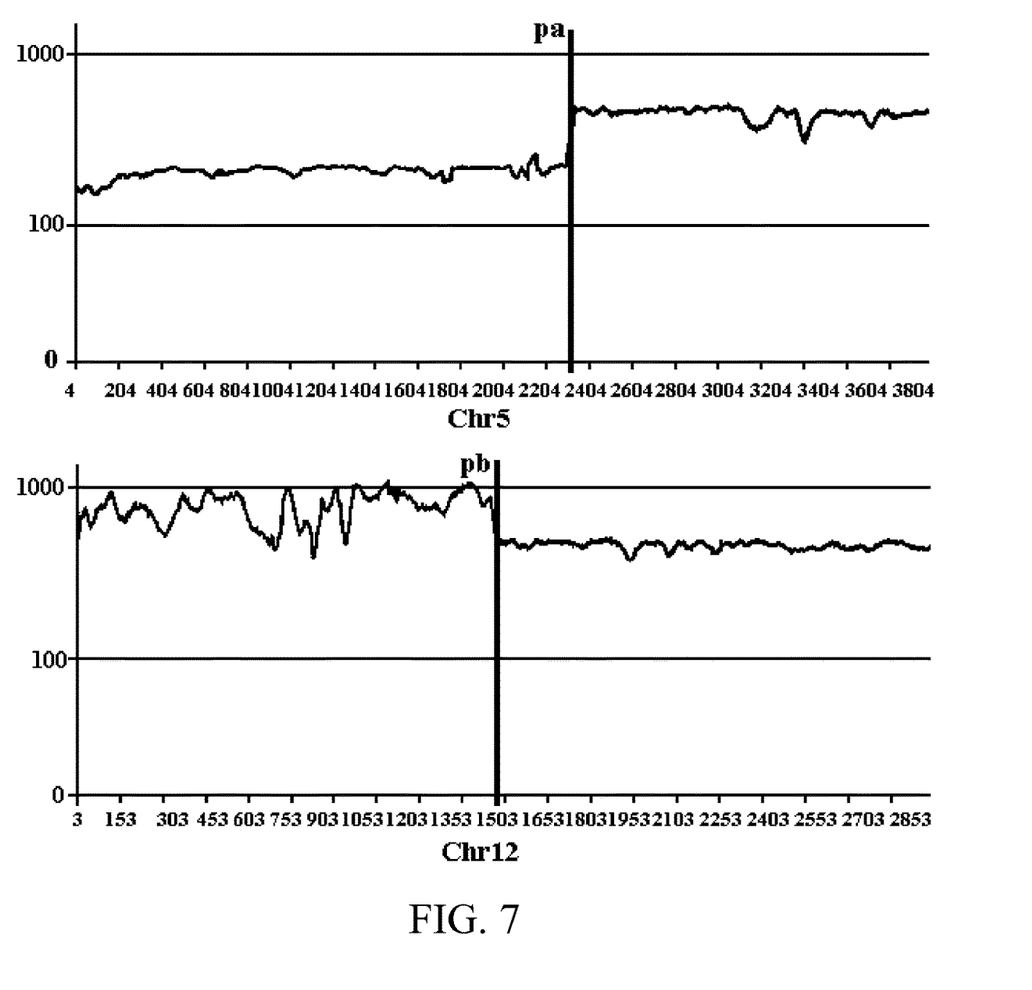
FIG. 7 is a schematic view of RPK for "SON" in Experimental Example 1 according to an embodiment of the present invention.

"SON":

numbering of two chromosomes on which paired result clusters reside: chr12, chr5 position ranges of two ends of paired result clusters: 14779618-14779968, 23314455-23314830 spans of two ends of paired result clusters: 350, 375 number of Read pairs supporting the pair of result clusters: 6 compactness (variance) of the left and right ends: 22.43, 18.44 whether the clusters are located in an N region: not range of breakpoints: chr12: above 14779968, chr5: below 23314455 variation in RPK of relevant regions on the chromosome—In FIG. 7, the horizontal axis represents the position (unit: 10 Kbp) on the chromosome, and the longitudinal axis represents RPK. The curve is plotted on basis of the data from SON.pair, and pa and pb represent the positions of breakpoints. It can be seen from FIG. 7 that the variation in RPK of "SON" is obvious. It can be known from review of the calculated RPK that the RPK in the forearm of chromosome 5 of SON is only 0.5 times of the average, and the RPK in the forearm of chromosome 12 is 0.5 time higher than the average.

It can be undoubtedly determined from the analysis results that balanced translocation occurs to "FA" and unbalanced translocation occurs to "SON". The range of breakpoints analyzed from the result of "FA" falls within 300 bp. To further carry out the study on breakpoint positions, a corresponding sequence is removed from the reference sequence HG19, and a primer is designed, for Sanger sequencing and validation by qPCR. The finally obtained accurate positions of breakpoints are Chr12:14780019, Chr5:23314435.

Experimental Example II

This example gives study on congenital heart disease. In this example, the target individual is a patient with congenital heart disease, and designated as "XX".

1. Whole-genome sequencing was conducted on the target individual at a low multiplier, in which the sequencing depth was 2.7.

2. Then, the sequencing result was aligned with the reference sequence HG19 by using the SOAP alignment software, to obtain XX.sin.

3. XX.sin was clustered, filtered, and analyzed, to obtain the following result clusters and relevant output parameters:

"XX":

numbering of two chromosomes on which paired result clusters reside: chr14, chr14 position ranges of two ends of paired result clusters: 73557040-73557288, 73670432-73670682 estimated length of repeat fragment: 113392 spans of two ends of paired result clusters: 248, 250 number of Read pairs supporting the pair of result clusters: 4 compactness (variance) of the left and right ends: 100.63, 100.59 whether the clusters are located in an N region: not range of breakpoints: chr14: 73556540-73557040, chr14: 73670682-73671182 (where the size of the range is estimated based on 1 time of L-lib, that is 500 bp)

It can be undoubtedly determined from the analysis result that a repetition of about 113 Kbp in length occurs to the chromosome 14 of "XX", and the repetition occurs in tandem. To further carry out the study on breakpoint positions, a corresponding sequence is removed from the reference sequence HG19, and a primer is designed, for Sanger sequencing and validation by qPCR. The multiplication ratio of qPCR is greater than 1, suggesting a repetition. The accurate positions of breakpoints finally obtained from Sanger sequencing are Chr14: 73557008, Chr14: 73670820, which confirms that a repetition of 113812 bp does occur to the chromosome 14 of "XX", and the repeat fragment is inserted at the end of the fragment in tandem.

The forgoing descriptions are merely preferred embodiments of the present invention, and it should be understood that these embodiments are provided for interpreting, instead of limiting the present invention. Variations may be made to particular embodiments above by those of ordinary skill in the art in accordance with the idea of the invention.

What is claimed is:

1. A method for detecting a chromosomal structural abnormality, comprising:
    (a) acquiring a whole genome sequencing result of a target individual or target individuals, wherein the sequencing result includes multiple pairs of Reads, each pair of Reads consists of two Read sequences located respectively at two ends of a chromosome fragment, and each pair of Reads is derived separately from the positive and negative strands of the corresponding chromosome fragment, or both from the positive or negative strand of the corresponding chromosome fragment;
    (b) aligning the sequencing result with a reference sequence, to obtain an abnormal match set and detect the chromosomal structural abnormality, wherein the abnormal match set includes:
        (i) a first type of Read pairs in which each of the two Read sequences of the first type of Read pair is matched to a different chromosome of the reference sequence;
        clustering the Read sequences in the abnormal match set based on the positions matched thereto, wherein each cluster contains single-end Read sequences from a group of Read pairs, and the corresponding other-end Read sequences reside in another cluster;
        filtering the clusters resulting from the clustering, including calculating the compactness of each cluster, excluding Read sequences located at the two ends of each cluster, and filtering out the clusters having a compactness above a preset compactness threshold, R-va, and the clusters paired therewith, wherein the compactness is indicated by variance of the position of each read in a cluster to the center of the cluster, and R-va is set such that the ranks of the variances in all the clusters fall within a lowermost interval of 2%-10%; and obtaining the filtered result clusters containing the first type of Read pairs to thereby determine the occurrence of translocation-type chromosomal structural abnormality;

(ii) a second type of Read pairs in which each of the two Read sequences of a second type of Read pair are matched to the same chromosome of the reference sequence, but the length L-pr of the chromosome fragment calculated according to the positions matched thereto is negative; and wherein the filtered result clusters containing the second type of Read pairs are obtained to thereby determine the occurrence of tandem repetition-type chromosomal structural abnormality; or (iii) a third type of Read pairs in which each of the two Read sequences of a third type of Read pair are matched to the same chromosome of the reference sequence, but the length L-pr of the chromosome fragment calculated according to the positions matched thereto is greater than a library size L-lib, and the deviation is above a preset length deviation threshold V-lib, wherein V-lib is 5%×L-lib to 15%×L-lib; and wherein the filtered result clusters containing the third type of Read pairs are obtained to thereby determine the occurrence of deletion-type chromosomal structural abnormality;

(c) designing primers for sequencing and/or quantitative polymerase chain reaction (qPCR) of the reference sequence based on the chromosomal structural abnormality detected in (b); and (d) sequencing the reference sequence and/or conducting qPCR on the reference sequence to validate the chromosomal structural abnormality.

2. The method according to claim 1, wherein the filtering of the clusters resulting from the clustering of (i) further comprises:

calculating the linear correlation of two paired clusters, and filtering out the paired clusters that have a linear correlation below a set linear correlation threshold, R-li, wherein R-li is set such that the ranks of the coefficients of correlation in all the clusters fall within an uppermost interval of 2%-10%; and/or aligning paired clusters with a preset control set comprising a plurality of normal samples, and filtering out the paired clusters that have a normal sample hitting count at or above a preset normal sample hitting count threshold, V-con, wherein the proportion of V-con to the number of normal samples in the control set is 3-10%.

3. The method according to claim 2, wherein during the calculation of the linear correlation of two paired clusters, the linear correlation is indicated by a coefficient of correlation.

4. The method according to claim 1, further comprising:

searching the result clusters containing the first type of Read pairs, if two adjacent Read sequences have opposite positions in respective Read pairs, taking the range between positions that the two Read sequences are matched to as a range of breakpoints; and if no such Read sequences exist, acquiring the position of an innermost Read sequence, and taking the range obtained by extending inward from the position by a preset length as a range of breakpoints.

5. The method according to claim 1, further comprising:

searching the result clusters containing the second type of Read pairs, taking the range between two positions matched thereto that are farthest in distance in the paired clusters as an occurrence range of repetition, and taking the range obtained by extending outward from the two positions respectively by a preset length as a range of breakpoints.

6. The method according to claim 1, further comprising:

searching the result clusters containing the third type of Read pairs, taking the range between two positions matched thereto that are closest in distance in the paired clusters as an occurrence range of deletion, and taking the range obtained by extending inward from the two positions respectively by a preset length as a range of breakpoints.

7. The method according to claim 1, wherein the aligning of the sequencing result with the reference sequence of (i) further comprises:

acquiring a normal match set, wherein the normal match set includes Read pairs in which each of the two Read sequences in the Read pair are matched to the same chromosome of the reference sequence, and the positive and negative strand relation of the positions matched thereto is in agreement with that in the Read pair, and the length L-pr of the chromosome fragment calculated according to the positions matched thereto deviates from the a library size L-lib used in sequencing by a value less than the preset length deviation threshold V-lib, wherein V-lib is from 5%×L-lib to 15%×L-lib; and statistically calculating the number RPU of Reads in the normal match set per unit length, and acquiring the variation of RPU compared with the average value, to assist in the determination of the occurrence of structural abnormities, wherein the variation of RPU compared with the average value is indicated by whether the variation of RPU is above a preset threshold V-rm, and V-rm is 10-30%.

8. The method according to claim 1, wherein the aligning of the sequencing result with the reference sequence of (i) further comprises:

acquiring an unmatch set, which includes Read sequences that are unable to match to the reference sequence, and includes paired unmatched Read sequences or single-end unmatched Read sequences; and after clustering and obtaining the resulting clusters, the method further comprises acquiring single-end Read sequences in a range set peripherally to the determined range of breakpoints, retrieving Read sequences paired therewith from the unmatch set as patch sequences, truncating all the patch sequences into N sections, wherein N is 2, aligning the sub-sequences obtained after truncating the patch sequences with the reference sequence again, and assembling the breakpoint region according to the result of normal match.

9. The method according to claim 1, wherein during the calculation of the compactness of each cluster of (i), 5 to 25% of the Read sequences located at the two ends of each cluster are excluded from calculation.

10. The method according to claim 1, wherein the library size L-lib used in sequencing is greater than or equal to 300 bp, and/or the length of the Read sequences is greater than or equal to 25 bp.

* * * * *